United States Patent
Stien

(10) Patent No.: US 7,438,818 B2
(45) Date of Patent: Oct. 21, 2008

(54) CROSS-LINKED POLYIMINE AND USE THEREOF FOR THE IMMOBILIZATION OF ACIDIC OR ELECTROPHILIC COMPOUNDS PRESENT IN A SOLUTION

(75) Inventor: Didier Stien, Cayenne (FR)

(73) Assignees: Centre National de la Recherche Scientifique, Paris (FR); Universite de Montpellier I, Montpellier (FR); Universite de Montpellier II, Montpellier (FR)

( * ) Notice: Subject to any disclaimer, the term of this patent is extended or adjusted under 35 U.S.C. 154(b) by 358 days.

(21) Appl. No.: 10/558,264

(22) PCT Filed: Apr. 29, 2004

(86) PCT No.: PCT/FR2004/001037

§ 371 (c)(1),
(2), (4) Date: Nov. 21, 2005

(87) PCT Pub. No.: WO2004/103516

PCT Pub. Date: Dec. 2, 2004

(65) Prior Publication Data

US 2007/0017872 A1 Jan. 25, 2007

(30) Foreign Application Priority Data

May 21, 2003 (FR) .................................. 03 06102

(51) Int. Cl.
*B01D 15/00* (2006.01)
*C07F 9/02* (2006.01)

(52) U.S. Cl. ....................................... 210/679; 558/146

(58) Field of Classification Search ................. 210/679; 558/146

See application file for complete search history.

(56) References Cited

U.S. PATENT DOCUMENTS 5,162,404 A  11/1992  Rainer
2004/0232081 A1*  11/2004  Boese et al. ................ 210/679

FOREIGN PATENT DOCUMENTS

CH         101 43 171         3/2003

OTHER PUBLICATIONS

Yoshida Hiroyuki et al. "Adsorption of Strong Acid on Polyaminated Highly Porous Chitosan: Equilibria", Ind. Eng. Chem. Res. 1994, vol. 33, pp. 854-959, XP002266337.
Database WPI, Section Ch, Week 198744, Derwent Publications Ltd., London, GB; Class A26, AN 1987-309423, XP002266338 and JP 62 216641 A (Nippon Shokubai Kagaku Kogyo Co Ltd), (Sep. 24, 1987).
PCT Search Report dated Sep. 15, 2004.

* cited by examiner

*Primary Examiner*—Chester T Barry
(74) *Attorney, Agent, or Firm*—Crowell & Moring LLP

(57) ABSTRACT

The invention relates to a process for immobilizing acidic or electrophilic compounds in a solution. The process is characterized in that it consists in bringing a crosslinked polyimine, which is insoluble in the medium and in which the imino groups are —NH-groups, into contact with said compounds and in then separating, by filtration, the modified polyimine obtained. The crosslinked polyimine comprises linear segments composed of —HN—$R^1$—NH—$R^2$—Ar—$R^3$-units in which $R^1$, $R^2$ and $R^3$ are identical or different alkylene or alkenylene groups and Ar represents an aromatic group. The process is of use for fixing undesirable compounds or for purifying acidic compounds.

13 Claims, No Drawings

CROSS-LINKED POLYIMINE AND USE THEREOF FOR THE IMMOBILIZATION OF ACIDIC OR ELECTROPHILIC COMPOUNDS PRESENT IN A SOLUTION

BACKGROUND OF THE INVENTION

1. Field of the invention:

The invention relates to a polymer material which can be used for trapping byproducts and excess reactants in a reaction medium.

2. Brief Description of the Related Art

During the performance of a chemical reaction in order to prepare a desired product, undesirable byproducts are often obtained and have to be removed. In addition, the reaction medium may comprise excess reactants which also have to be removed. The use has been envisaged of polymers on which the undesirable compounds may become fixed.

The proposal has been made to use polyimines immobilized on a support for removing acidic compounds in an organic solvent. For example, DE 101 43 171 discloses a process for the preparation of a material for the removal of acids from an aprotic organic liquid, said material being composed of a polyalkyleneimine fixed to a support, for example silica. Yoshida Hiroyuki (Ind. Eng. Chem. Res.; vol. 33, No. 4, April 1994, pp. 854-859) describes the adsorption of a strong acid on a weakly basic exchanger composed of a polyethyleneimine fixed to a highly porous chitosan. JP 62216641 discloses a polyethyleneimine having a molecular weight of greater than 5000 adsorbed on a support (for example, a porous resin) and its use as adsorbent for strong acids, surfactants or heavy metals. The polyimine is adsorbed on the porous resin by immersion of the resin in a polyimine solution. It is thus a polyimine soluble in organic solvents which is immobilized on a support. The document U.S. Pat. No. 5,162,404 discloses a sponge composed of cellulose and an "immobilized" polyethyleneimine fixed to the cellulose. The polyethyleneimine is a water-soluble branched polymer which comprises primary, secondary or tertiary amine groups separated by —$CH_2CH_2$- groups and which is rendered insoluble by crosslinking using a halogenated or nonhalogenated carboxylic acid or a polyhalogenated aliphatic compound of low molecular weight which reacts with the N atoms of the amine groups. In all these processes, however, there are a number of disadvantages to the immobilization of the polyimine on a support. First, the preparation of the immobilization support requires two stages (preparation of the polyimine and then fixing of the polyimine on the support), which increases the production costs. Secondly, for a given amount of support, the number of working functional groups is markedly lower when the polyimine is fixed to a support.

The proposal has been made to use an insoluble polymer as immobilization agent for a compound in solution. The polymers conventionally used are poly(styrene-divinyl-benzene)s carrying reactive functional groups which make possible the fixing of the compounds to be removed (cf. WO97/42230 and J. Chem. Soc., Perkin Trans. 1, 2000, p. 4133-4195). However, the polymers of this type cannot be used in aqueous media or in methanol. In addition, they have a relatively low level of active functional groups, which limits their performance.

SUMMARY OF THE INVENTION

The aim of the present invention is to provide a process for efficiently removing, using an insoluble immobilization agent, undesirable acidic or electrophilic compounds in water and the organic solvents generally used for the synthesis of organic compounds.

A subject matter of the invention is a process for immobilizing acidic or electrophilic compounds present in a solvent. It is characterized in that it consists in bringing a crosslinked polyimine, in which the imino groups are —NH—groups, into contact with said compounds, said crosslinked polyimine being insoluble in said solvent, and in separating, by filtration, the modified polyimine obtained.

DETAILED DESCRIPTION OF THE PREFERRED EMBODIMENTS

The contacting operation can advantageously be carried out at ambient temperature. The duration of the contact varies according to the nature of the compounds. Generally, a duration of between 1 hour and approximately 10 hours is sufficient.

A crosslinked polyimine which is particularly appropriate for the implementation of the process of the invention comprises linear segments composed of —HN—$R^1$—NH—$R^2$—Ar—$R^3$- units in which $R^1$, $R^2$ and $R^3$ are identical or different alkylene or alkenylene groups and Ar represents an aromatic group.

$R^1$, $R^2$ and $R^3$ are preferably alkylene or alkenylene groups having from 1 to 10 carbon atoms. The aromatic group Ar is preferably a φ or φ-φ group in which φ represents a phenyl optionally carrying one or more substituents. The substituents of the phenyl group can be chosen from alkyl, aryl, alkyloxy, alkoxycarbonyl, halogen or $NO_2$ groups.

The presence of phenyl groups in the repeat units confers amphiphilic properties on the polyimine which allow it to be used both in hydrophobic media and in hydrophilic media.

In a polyimine used for the process of the present invention, the crosslinking nodes can be, for example, of the C($R_4$NH—$R^2$—Ar—$R^3$—)$_{4-n}$($R^4NH_2$)$_n$ or N($R^4$NH—$R^2$—$^{Ar-R}{}_3$—)$_3$ type in which $R^4$ represents an alkylene group preferably having from 1 to 10 carbon atoms and n is 0 or 1.

A polyimine as defined above has a very high content of NH groups. For example, it is of the order of 11 mmol/g when $R^1$ and $R^4$ are —$CH_2CH_2$—and $R^2$ and $R^3$ are —$CH_2$—. In addition, although insoluble in water and in the organic solvents normally used for various chemical reactions, it swells when it is placed in such solvents, that is to say that it has an ability to accept solvent and reactant molecules within the molecular mesh. The active NH sites of the polyimine are thus accessible and can react with various compounds, in particular with inorganic or organic acids and with electrophilic compounds. This property is taken advantage of in trapping compounds of this nature which are present in a reaction medium and which are undesirable. The high content of NH groups is confirmed by the IR spectrum of the polyimine, which exhibits a very broad band at approximately 3300-3400 $cm^{-1}$, characteristic of the NH groups.

The crosslinked polyimines which can be used in the process of the invention can be prepared by a single-stage process which consists in polycondensing a diamine $H_2N$—$R^1$—$NH_2$ with a dihalide X—$R^2$—Ar—$R^3$—X in an organic solvent in the presence of a crosslinking agent and of an agent capable of trapping the hydrohalic acid formed. $R^1$, $R^2$, $R^3$ and Ar are as defined above.

It is preferable to use a diamine and a crosslinking agent which have an equivalent reactivity with respect to the dihalide in order to obtain a random distribution of the crosslinking nodes. For this purpose, it is advantageous to choose a tetramine N($R^4NH_2$)$_3$ or C($R^4NH_2$)$_4$. The crosslinking agent/ diamine molar ratio is preferably less than or equal to 4 mol %. Under these conditions, the polymer obtained remains completely insoluble in the solvents (water or organic solvents) but it swells well in said solvents (with the exception of alkanes).

Preference is given, among dihalides, to dichlorides.

The organic solvent used for preparing a polyimine is preferably chosen from those which make it possible to dissolve the monomers and to cause the growing polymer to swell. Mention may be made, by way of examples, of toluene and DMF.

Mention may be made, as agent capable of trapping the hydrohalic acid, of tertiary amines, for example triethylamine or diisopropylethylamine.

The process of the invention can be employed for the trapping and removal of inorganic acids, of organic acids or of various electrophilic compounds which are formed as byproducts during a reaction or which are reactants used in excess in a reaction mixture.

The trapping of an inorganic acid HX (X is, for example, Cl, $HSO_4$, $NO_3$, $H_2PO_4$, Br or I) or an organic acid HX (X is, for example, a carboxylate or a sulfonate) is carried out according to the following reaction scheme, in which the compound 4 represents a crosslinked polyimine according to the invention:

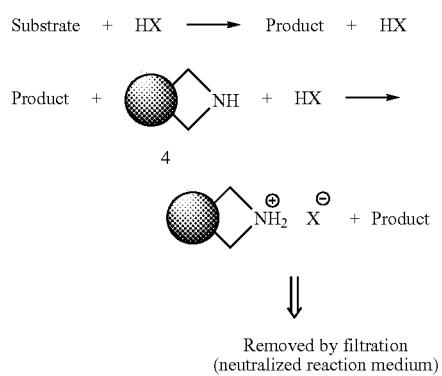

As the polyimine is amphiphilic, it can be used to trap inorganic acids in the aqueous phase as in the organic phase. Thus, the reaction medium comprising the desired product is neutralized and freed from neutralization salts by simple filtration. This facilitates is the isolation of the desired product insofar as stages of extraction at different pH values are avoided.

The trapping of an electrophilic compound is carried out according to the following reaction scheme:

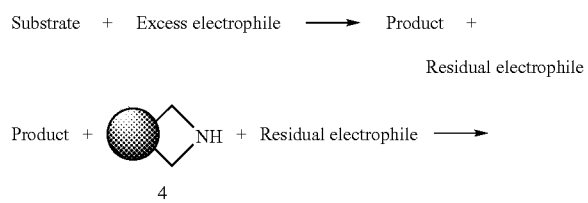

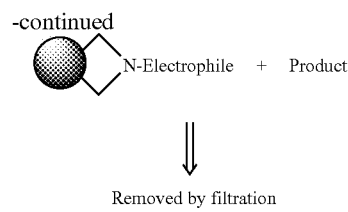

The use of an excess of reactant in a chemical reaction makes it possible to obtain better degrees of conversion and consequently better yields of the desired product. However, the presence of residual electrophilic reactant at the end of the reaction interferes with the purification. A crosslinked polyimine according to the present invention reacts with the excess electrophilic compound in the same way as a secondary amine in solution and a covalent bond is formed between the two entities. The excess electrophilic compound is thus destroyed and the polyimine-electrophile entity can be removed from the reaction medium by simple filtration, which simplifies the stages of isolation and purification of the desired product.

In addition, the process of the invention can be used for the purification of acids by temporary attachment, according to the following reaction scheme:

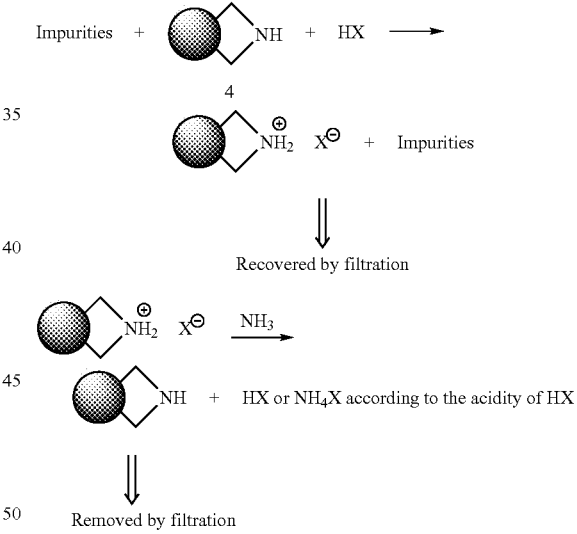

Any protic entity HX having a pKa of the HX/X⁻ pair which is substantially lower (2 to 3 pKa units) than that of a secondary amine can be bonded temporarily to the polyimine in order to make possible its purification by filtration. A subsequent treatment with an excess of base will liberate the desired product. If the base chosen is volatile (for example $NH_3$), the product can be recovered in the pure state after simple evaporation, in the HX or $NH_4X$ form, depending on the acidity of HX. In this case also, the temporary fixing of the desired product to the polyimine makes it possible to avoid tedious stages of extraction at different pH values.

The present invention is described in more detail by the examples given below, to which, however, it is not limited.

Example 1

Synthesis of polyimine

A mixture of ethylenediamine (1) (2 ml, 0.03 mol), of tris(2-aminoethyl)amine (3) (90 µl, 0.6 mmol), of 1,4-bis(chloromethyl)benzene (2) (5.25 g, 0.03 mol) and of triethylamine (12.5 ml, 0.09 mol) in toluene was prepared and then this mixture was brought to reflux for approximately ten hours with stirring. After cooling, the polymer (4) formed was recovered by filtration, washed successively with a 1M aqueous sodium hydroxide solution, with methanol, with ethyl acetate and with hexane, and then dried under vacuum. 4.4 g of dry polyimine were thus obtained, corresponding to a yield of 90%.

The reaction scheme corresponding to the achievement of the repeat units between the crosslinking nodes is shown below:

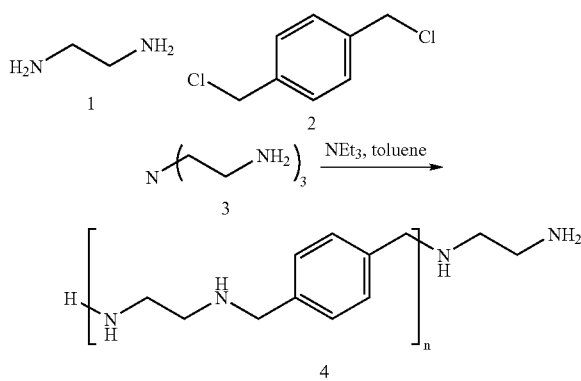

The polymer obtained was subjected to infrared analysis using a milled sample with KBr. The positions of the lines on the IR spectrum in cm$^{-1}$ are as follows: 3370 (N—H), 2930, 2810, 1610, 1509, 1458, 1364, 1087 (C—N), 822. The presence of a broad absorption band at 3370 cm$^{-1}$, due to the stretching of the N—H bond, clearly shows that the product analyzed comprises a high proportion of NH groups.

The degree of swelling (in ml/g) in various solvents is given below:

| Hexane | Dichloromethane | THF | Methanol | DMF | Water |
|---|---|---|---|---|---|
| 3.0 | 4.8 | 4.2 | 5.6 | 4.4 | 5.0 |

These values show that the polyimine can be regarded as amphiphilic. It can consequently be used in a larger number of applications than commercially available polystyrene polymers, such as for the trapping of undesired compounds. This is because polystyrene polymers are completely hydrophobic and they swell neither in water nor in methanol (<2 ml/g of resin).

The reactivity of the NH groups was determined by bringing the polyimine into contact with di(tert-butyl) dicarbonate (Boc$_2$O), which is a relatively hindered and weakly reactive electrophilic reactant. The polyimine was treated with an excess of Boc$_2$O. The reaction was carried out in CDCl$_3$. The amount of Boc$_2$O which could be "absorbed" by the polyimine is determined by subtraction of the amount remaining in solution from the initial amount, the measurements being carried out by proton NMR. This process gives a direct reading of the effective content of amine in the polyimine. Thus, the calculation of the theoretical content expected on the basis of the polymer mesh shows that there should be 12.3 mmol of amines per gram. The measurement of the effective content for the trapping of Boc$_2$O gives a value of 10.9 mmol of NH per gram of resin, which means that almost 90% of the NH groups are accessible, even for a relatively unreactive electrophile.

Example 2

Synthesis of Polyimine

A mixture of 1,7-heptanediamine (1.3 g, 10 mmol), of tris(2-aminoethyl)amine (30 pmol, 0.2 mmol), of 1,4-bis(chloromethyl)benzene (1.75 g, 10 mmol) and of diisopropylethylamine (5.2 ml, 30 mmol) in DMF (5 ml) was prepared and then this mixture was brought to 80° C. for 48 hours with stirring. After cooling, the polymer formed was recovered by filtration, washed successively with a 2M aqueous sodium hydroxide solution, with distilled water, with methanol, with ethyl acetate and with dichloromethane, and then dried under vacuum for approximately ten hours. 2 g of dry polyimine were thus obtained, corresponding to a yield of 85%.

Theoretical content=8.7 mmol/g; Effective content for the trapping of Boc$_2$O=7.5 mmol/g.

IR (milled sample with KBr, in cm$^{-1}$): 3325 (N—H stretch), 2930, 2830, 1595, 1458, 1364.

Example 3

Synthesis of Polyimine

A mixture of 1,3-propanediamine (0.83 ml, 10 mmol), of tris(2-aminoethyl)amine (30 µmol, 0.2 mmol), of 1,4-bis(chloromethyl)benzene (1.75 g, 10 mmol) and of diisopropylethylamine (5.2 ml, 30 mmol) in DMF (5 ml) was prepared and then this mixture was brought to 80° C. for 48 hours with stirring. After cooling, the polymer formed was recovered by filtration, washed successively with a 2M aqueous sodium hydroxide solution, with distilled water, with methanol, with ethyl acetate and with dichloromethane, and then dried under vacuum for approximately ten hours. 1.6 g of dry polyimine were thus obtained, corresponding to a yield of 91%.

Theoretical content=12.3 mmol/g; Effective content for the trapping of Boc$_2$O=11.5 mmol/g.

IR (milled sample with KBr, in cm$^{-1}$): 3360 (N—H stretch), 2930, 2830, 1610, 1458, 1364.

Example 4

Trapping of Sulfuric Acid in the Aqueous Phase

A crosslinked polyimine obtained according to the procedure of example 1 (64 mg, 0.64 mmol, ≈3 eq.) was added to a solution of sulfuric acid (12.0 mg, 0.122 mmol) in distilled water (0.5 ml, C=0.24, M≈0.5 N, pH=0.3). The resin swelled well and, after one hour, the pH of the solution was in the vicinity of 6. The concentration of protons is thus 10$^{-6}$N, which means that the trapping of the H$^+$ ions is quantitative (>99.9%).

Example 5

Trapping of HCl in the Aqueous Phase crosslinked polyimine prepared according to example 1 (52 mg, 0.52 mmol, ≈3 eq.) was added to a solution of hydrochloric acid (18 mg, 35%, 0.173 mmol) in distilled water (0.5 ml, C=0.345M/N, pH =0.46). The resin swelled well and, after one hour, the pH of the solution was in the vicinity of 6. The concentration of protons is thus $10^{-6}$N, which means that, here again, the trapping of the H$^+$ ions is quantitative (>99.9%).

Example 6

Trapping of Para-toluenesulfonic Acid (CH$_2$Cl$_2$)

A mixture of p-toluenesulfonic acid monohydrate (TsOH) (7.5 mg, 39.4 µmol) and of pentamethylbenzene (6.6 mg, 44.5 µmol, internal standard) in solution in dichloromethane (300 µl) was treated with 3 equivalents of polyimine prepared according to example 1 (12 mg, 120 µmol). After filtering and evaporating, it was observed, by NMR, that the TsOH/pentamethylbenzene ratio was 0.02. Thus, only 0.89 µmol of TsOH remains in the medium, i.e. only 2% of the initial amount.

Example 7

Trapping of Para-toluenesulfonic Acid (Methanol)

A mixture of TsOH monohydrate (8.4 mg, 44.2 µmol) and of pentamethylbenzene (6.8 mg, 45.85 µmol, internal standard) in solution in CD$_3$OD (300 µl) was treated with 3 equivalents of polyimine prepared according to example 1 (13.5 mg, 14 µmol). After filtering, it was observed, by NMR, that the TsOH/pentamethylbenzene ratio was 0.01. Thus, only 0.46 µmol of TsOH remains in the medium, i.e. only 1% of the initial amount.

Example 8

Trapping of an Electrophilic Compound

Dibenzylamine (96 µl, 0.5 mmol), in solution in CDCl$_3$ (2 ml) comprising a small amount of dimethylaminopyridine (DMAP) as catalyst (6 mg, 0.05 mmol), was treated with an excess of Boc$_2$O (218 mg, 1 mmol) to produce the carbamate (PhCH$_2$)$_2$N—Boc. After 1 hour, a crosslinked polyimine prepared according to example 1 (140 mg, 1.5 mmol of NH, 3 equivalents with respect to the excess of the electrophilic compound Boc$_2$O) was added. The reaction mixture was stirred for approximately ten hours at ambient temperature and then the polyimine was removed by filtration through cotton wool. The $^1$H NMR spectrum shows that the excess Boc$_2$O has indeed been removed by this postreaction treatment.

What is claimed is:

1. A crosslinked polyimine comprising linear segments composed of —HN—R$^1$—NH—R$^2$—Ar—R$^3$— units in which R$^1$, R$^2$ and R$^3$ are identical or different alkylene or alkenylene groups and Ar represents an aromatic group.

2. The polyimine as claimed in claim 1, wherein the alkylene or alkenylene groups have from 1 to 10 carbon atoms.

3. The polyimine as claimed in claim 1, wherein Ar is a φ or φ-φ group in which φ represents a phenyl optionally carrying one or more substituents.

4. The polyimine as claimed in claim 1, wherein the substituents of the phenyl group are chosen from alkyl, aryl, alkyloxy, alkoxycarbonyl, halogen or NO$_2$ groups.

5. The polyimine as claimed in claim 1, wherein the crosslinking nodes are of the N(R$^4$NH—R$^2$—Ar—R$_3$—)$_3$ or C(R$^4$NH—R$^2$—Ar —R$^3$)$_{4-n}$ (R$^4$NH$_2$)$_n$ or type in which R$^4$ represents an alkylene group and n is 0 or 1.

6. The polyimine as claimed in claim 5, wherein the alkylene group has from 1 to 10 carbon atoms.

7. The polyimine as claimed in claim 1, wherein it has a content of NH groups of the order of 11 mmol/g.

8. A process for the removal of organic acid or inorganic acids present in a hydrophobic reaction medium or in a hydrophilic reaction medium, which comprises bringing a crosslinked polyimine according to claim 1 in contact with said acid compounds and then separating a modified polyimine product.

9. A process for the removal of electrophilic compounds present in a hydrophobic reaction medium or in a hydrophilic reaction medium, which comprises bringing a crosslinked polyimine according to claim 1 in contact with said electrophilic and then separating a modified polyimine product.

10. The process of claim 8, wherein the process further comprises treating the modified polyimine product with a base.

11. A process for immobilizing acidic or electrophilic compounds present in a solvent, wherein the process comprises bringing a crosslinked polyimine, into contact with said compounds, and in separating, by filtration, the modified polyimine obtained, wherein the crosslinked polyimine is a polyimine according to claim 1.

12. The process as claimed in claim 1, wherein the contacting operation is carried out at ambient temperature.

13. The process as claimed in claim 1, wherein the duration of the contact is between 1 hour and approximately 10 hours.

* * * * *